US009562857B2

(12) United States Patent
Debevec et al.

(10) Patent No.: US 9,562,857 B2
(45) Date of Patent: Feb. 7, 2017

(54) SPECULAR OBJECT SCANNER FOR MEASURING REFLECTANCE PROPERTIES OF OBJECTS

(71) Applicants: Paul E. Debevec, Culver City, CA (US); Xueming Yu, Arcadia, CA (US); Graham Leslie Fyffe, Los Angeles, CA (US); Abhijeet Ghosh, London (GB)

(72) Inventors: Paul E. Debevec, Culver City, CA (US); Xueming Yu, Arcadia, CA (US); Graham Leslie Fyffe, Los Angeles, CA (US); Abhijeet Ghosh, London (GB)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 112 days.

(21) Appl. No.: 14/212,751

(22) Filed: Mar. 14, 2014

(65) Prior Publication Data

US 2014/0268160 A1 Sep. 18, 2014

Related U.S. Application Data

(60) Provisional application No. 61/783,115, filed on Mar. 14, 2013.

(51) Int. Cl.
*G01N 21/55* (2014.01)
*G01B 11/30* (2006.01)
*G01B 11/25* (2006.01)

(52) U.S. Cl.
CPC ............... *G01N 21/55* (2013.01); *G01B 11/25* (2013.01); *G01B 11/30* (2013.01)

(58) Field of Classification Search
CPC ....... G01B 11/24; G01B 11/245; G01B 11/25; G01B 11/2518; G01B 11/306; G01B 11/2545; G01B 11/2513; G01B 11/2531; G01B 11/254; G01B 11/30; G01B 11/303; G01N 21/55; G01N 21/57; G01N 21/88; G01N 21/8803; G01N 21/8806; G01N 21/956; G01S 17/89

See application file for complete search history.

(56) References Cited

U.S. PATENT DOCUMENTS 6,853,745 B1 2/2005 Jacobs et al.
2004/0227948 A1 11/2004 Debevec et al.
(Continued)

OTHER PUBLICATIONS

Adato, Y. et al. 2007. Toward a theory of shape from specular flow, In Proc. IEEE International Conference on Computer Vision, 1-8.
(Continued)

*Primary Examiner* — Gordon J Stock, Jr.
(74) *Attorney, Agent, or Firm* — McDermott Will & Emery LLP

(57) ABSTRACT

An apparatus to measure surface orientation maps of an object may include a light source that is configured to illuminate the object with a controllable field of illumination. One or more cameras may be configured to capture at least one image of the object. A processor may be configured to process the image(s) to extract the reflectance properties of the object including an albedo, a reflection vector, a roughness, and/or anisotropy parameters of a specular reflectance lobe associated with the object. The controllable field of illumination may include limited-order Spherical Harmonics (SH) and Fourier Series (FS) illumination patterns with substantially similar polarization. The SH and FS illumination patterns are used with different light sources.

20 Claims, 7 Drawing Sheets

(56) References Cited

U.S. PATENT DOCUMENTS

| | | |
|---|---|---|
| 2006/0214931 A1 | 9/2006 | Snyder et al. |
| 2009/0157649 A1 | 6/2009 | Papadakis et al. |
| 2009/0226049 A1 | 9/2009 | Debevec et al. |
| 2010/0328677 A1* | 12/2010 | Debevec ............... G01N 21/55 356/600 |
| 2011/0292405 A1 | 12/2011 | Dunn et al. |

OTHER PUBLICATIONS

Blake, A. et al. 1992. Geometry from specularities, in Physics-Based Vision, Principles and Practice: Shape Recovery, L. B. Wolff, S. A. Shafer, and G. E. Healey, Eds. Jones and Bartlett Publishers, Inc., USA, ch., 277-286.
Bonfort, T. et al. 2003. Voxel carving for specular surfaces, In Proc. IEEE International Conference on Computer Vision, 591-596.
Chen, T. et al. 2006. Mesostructure from specularity, in IEEE Computer Society Conference on Computer Vision and Pattern Recognition, Jun. 17-22, 2006, 1825-1832.
Dana, K. J. et al. 1999, Reflectance and texture of real-world surfaces. ACM Trans. Graph. 18, 1 (Jan.), 1-34.
Debevec, P. et al. 2000. Acquiring the reflectance field of a human face, in Proceedings of ACM SIG GRAPH 2000, 145-156.
Dong, Y. et al. 2010. Manifold bootstrapping for SVBRDF capture, ACM Trans. Graph. 29 (July), 98:1-98-98:10.
Francken, Y. et al. 2008. High quality mesostructure acquisition using specularities, in Conference on Computer Vision and Pattern Recognition (CVPR 2008), IEEE Computer Society, 1-7.
Gardner, A. et al. 2003. Linear light source reflectometry, in Association for Computing Machinery, Transactions on Graphics, Proceedings of ACM SIGGRAPH 2003, vol. 22, No. 3, Jul. 2003, 749-758.
Ghosh, A. et al. 2009. Estimating specular roughness and anisotropy from second order spherical gradient illumination, Comput. Graph. Forum 28, 4, 1161-1170.
Ghosh, A. et al. 2010. A basis illumination approach to BRDF measurement, Int. J. Comput. Vision 90, 2 (Nov.), 183-197.
Hawkins, T. et al. 2005. A dual light stage, in Proc. Eurographics Symposium on Rendering, 91-98.
Holroyd, M. et al. 2008. A photometric approach for estimating normal and tangents, ACM Trans. Graph. 27, 5 (Dec.), 133:1-133:9.
Holroyd, M. et al. 2010. A coaxial optical scanner for synchronous acquisition of 3d geometry and surface reflectance. ACM Trans. Graph. 29, 4 (July), 99:1-99:12.
Ihrke, I. et al. 2010. Transparent and specular object reconstruction. Computer Graphics Forum 29, 8, 2400-2426.
Ikeuchi, K. 1981, Determining surface orientations of specular surfaces by using the photometric stereo method. IEEE Trans. Pattern Anal. Mach. Intell. 3, 6 (June), 661-669.
Lamond, B. et al. 2009. Image-based separation of diffuse and specular reflections using environmental structured illumination, in Proc. IEEE International Conf. Computational Photography, Apr. 16-17, 2009, San Francisco, CA, 1-8.
Lensch, H.P.A. et al. 2003. Image-based reconstruction of spatial appearance and geometric detail, ACM TOG 22, 2, 234-257.
Ma, W.-C et al. 2007. Rapid acquisition of specular and diffuse normal maps from polarized spherical gradient illumination. In Rendering Techniques, 183-194.
McAllister, D.K. 2002, A generalized surface appearance representation for computer graphics, PhD thesis, The University of North Carolina at Chapel Hill. AAI3061704.
Nayar, S. et al. 1990. Determining shape and reflectance of hybrid surfaces by photometric sampling, IEEE Trans. Robotics and Automation 6, 4, 418-431.
Ren, P. et al. 2011. Pocket reflectometry, ACM Trans. Graph. 30, 4 (July), 45:1-45:10.
Sato, Y. et al. 1997. Object shape and reflectance modeling from observation, in Proceedings of the 24th annual conference on Computer graphics and interactive techniques, ACM Press/Addison-Wesley Publishing Co., New York, NY, USA, SIG-GRAPH '97, 379-387.
Tarini, M. et al. 2005. 3D acquisition of mirroring objects using striped patterns, Graphical Models 67, 4, 233-259.
Tunwattanapong, B. et al. 2013. Acquiring reflectance and shape from continuous Spherical Harmonic illumination, ACM Trans. Graph. 32, 4, Article 109 (Jul. 2013).
Wang, C.-P. et al. 2011. Estimating dual-scale properties of glossy surfaces from step-edge lighting. ACM Trans. Graph. (Proc. SIGGRAPH Asia) 30, 6.
Westin, S.H. et al. 1992. Predicting reflectance functions from complex surfaces, SIG-GRAPH Comput. Graph. 26, 2 (July), 255-264.
Weyrich, T. et al. 2009, Principles of appearance acquisition and representation, Foundations and Trends in Computer Graphics and Vision, vol. 4, No. 2 (Feb.), 75-191.
Woodham, R.J. 1980. Photometric method for determining surface orientation from multiple images, Optical Engineering 19, 1, 139-144.
Zickler, T. et al. 2006, Reflectance sharing: Predicting appearance from a sparse set of images of a known shape, PAMI 28, 8, 1287-1302.
Ghosh, A. et al. 2011. Multiview Face Capture Using Polarized Spherical Gradient Illumination. ACM Transactions on Graphics (TOG)—Proceedings of ACM SIGGRAPH Asia 2011, vol. 30, No. 6, Dec. 2011, Article No. 129 (Retrived online by ISA/US on Jun. 28, 2014 at <file:///U:/14-28727/PCT1428727_Multiview_SIG-GRAPHAsia_2011.pdf>).
International Search Report and Written Opinion of the International Searching Authority (US), dated Jul. 24, 2014, for counterpart PCT Application PCT/US2014/028727, entitled "Specular Object Scanner for Measuring Reflectance Properties of Objects," filed Mar. 14, 2014.

* cited by examiner

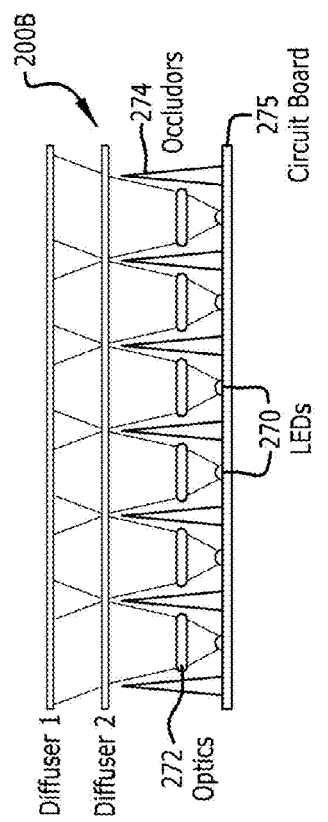
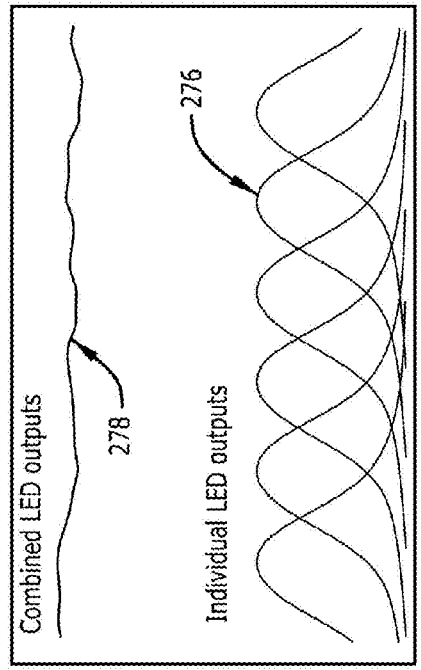
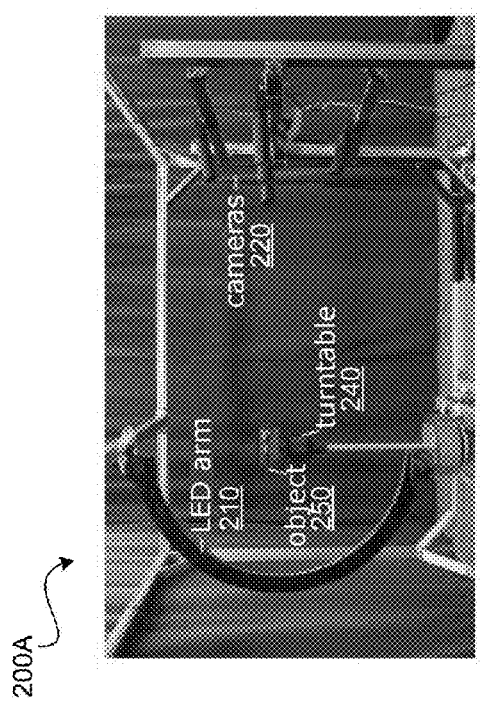
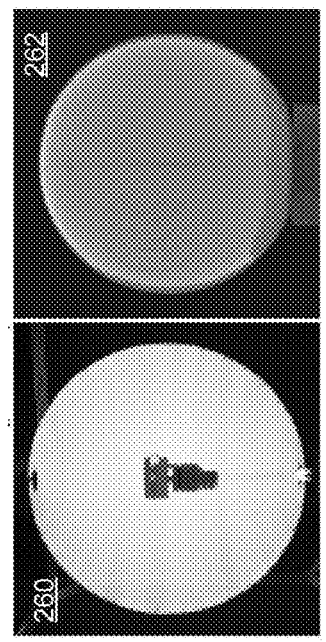
FIG. 2B
FIG. 2A
FIG. 2C

SPECULAR OBJECT SCANNER FOR MEASURING REFLECTANCE PROPERTIES OF OBJECTS

CROSS-REFERENCE TO RELATED APPLICATION

This application is based upon and claims priority to U.S. provisional patent application 61/783,115 entitled "Specular Object Scanner That Creates Controllable Illumination To Capture Data and Measure Properties Of Translucent, Transparent, And Reflective Objects" filed Mar. 14, 2013. The entire content of this application is incorporated herein by reference.

BACKGROUND

Technical Field

This disclosure relates to object scanners, in particular, but not restricted to a specular object scanner for measuring reflectance properties of objects.

Description of Related Art

An extensive body of work in the graphics and vision literature addresses the acquisition of geometry and reflectance from images under controlled and uncontrolled lighting conditions. Two recent overviews are Weyrich, T., Lawrence, J., Lensch, H. P. A., Rusinkiewicz, S., and Zickler, T. 2009, *Principles of appearance acquisition and representation*, Found. Trends. Comput. Graph. Vis. 4, 2 (Feb.), 75-191, which covers a wide variety of techniques for acquiring and representing BRDFs and Spatially Varying BRDFs (SVBRDFs) over object surfaces, and Ihrke, I., Kutulakos, K. N., Lensch, H. P. A., Magnor, M., and Heidrich, W. 2010, *Transparent and specular object reconstruction*, Computer Graphics Forum 29, 8, 2400-2426, which focused on the acquisition of on purely specular and transparent objects.

SVBRDFs can be captured exhaustively using point light sources (e.g. Dana, K. J., Van Ginneken, B., Nayar, S. K., and Koen Derink, J. J. 1999, Reflectance and texture of real-world surfaces. ACM Trans. Graph. 18, 1 (Jan.), 1-34; McAllister, D. K. 2002, *A generalized surface appearance representation for computer graphics*, PhD thesis, The University of North Carolina at Chapel Hill. AAI3061704, but this requires a large number of high-dynamic range photographs to capture every possible combination of incident and radiant angle of light. Similar to the disclosed approach, many techniques (e.g. Debevec, P., Hawkins, T., Tchou, C., Duiker, H.-P., Sarokin, W., and Sagar, M. 2000, *Acquiring the reflectance field of a human face*, in Proceedings of ACM SIG GRAPH 2000, 145-156; Gardner, A., Tchou, C., Hawkins, T., and Debevec, P. 2003, *Linear light source reflectometry*, in ACM TOG, 749-758.); Holroyd, M., Lawrence, J., Humphreys, G., and Zick LER, T. 2008, *A photometric approach for estimating normal and tangents*, ACM Trans. Graph. 27, 5 (Dec.), 133:1-133:9; Ren, P., Wang, J., Snyder, J., Tong, X., and Guo, B. 2011. Pocket reflectometry, ACM Trans. Graph. 30, 4 (Jul.), 45:1-45:10 look instead at BRDF slices of spatially-varying materials observed from a single viewpoint to infer parameters of a reflectance model, which can be used to extrapolate reflectance to novel viewpoints. Other approaches Sato, Y., Wheeler, M. D., and Ikeuchi, K. 1997, *Object shape and reflectance modeling from observation*, in Proceedings of the 24th annual conference on Computer graphics and interactive techniques, ACM Press/ Addison-Wesley Publishing Co., New York, N.Y., USA, SIGGRAPH '97, 379-387; Lensch, H. P. A., Kautz, J., Goesele, M., Heidrich, W., and Seidel, H.-P. 2003, *Image-based reconstruction of spatial appearance and geometric detail*, ACM TOG 22, 2, 234-257; Zickler, T., Ramamoorthi, R., Enrique, S., and Bel Humeur, P. N. 2006, *Reflectance sharing: Predicting appearance from a sparse set of images of a known shape.*, PAMI 28, 8, 1287-1302; Holroyd, M., Lawrence, J., and Zickler, T. 2010, *A coaxial optical scanner for synchronous acquisition of 3d geometry and surface reflectance*, ACM Trans. Graph. 29, 4 (Jul.), 99:1-99:12 use sparse sets of viewpoint and lighting directions and extrapolate BRDFs per surface point assuming that the reflectance varies smoothly over the object. This approach is also used by Dong, Y., Wang, J., Tong, X., Snyder, J., Lan, Y., Ben Ezra, M., and Guo, B. 2010, *Manifold bootstrapping for SVBRDF capture*, ACM Trans. Graph. 29 (Jul.), 98:1-98:10, which employs a dedicated BRDF measurement system to sample representative surface BRDFs, which are extrapolated to the surface of the entire object based on its appearance under a moderate number of environmental lighting conditions. None of these techniques, however, produces independent measurements of diffuse and specular reflectance parameters for each observed surface point, and thus may miss important surface reflectance detail.

Ikeuchi, K. 1981, *Determining surface orientations of specular surfaces by using the photometric stereo method*, IEEE Trans. Pattern Anal. Mach. Intell. 3, 6 (Jun.), 661-669 extended the original photometric stero approach of Woodham, R. J. 1980, *Photometric method for determining surface orientation from multiple images*, Optical Engineering 19, 1, 139-144 to specular surfaces, using a set of angularly varying area light sources to estimate the specular surface orientation. Nayar, S., Ikeuchi, K., and Kanade, T. 1990, *Determining shape and reflectance of hybrid surfaces by photometric sampling*, IEEE Trans. Robotics and Automation 6, 4, 418-431 used an extended light source technique to measure orientations of hybrid surfaces with both diffuse and specular reflectance, but they did not characterize the BRDF of the specular component. Gardner, A., Tchou, C., Hawkins, T., and Debevec, P. 2003, *Linear light source reflectometry*, in ACM TOG, 749-758.; Holroyd, M., Lawrence, J., Humphreys, G., and Zick L E R, T. 2008, *A photometric approach for estimating normal and tangents*, ACM Trans. Graph. 27, 5 (Dec.), 133:1-133:9 employed a moving linear light source to derive BRDF models of spatially-varying materials, including highly specular materials, but still required hundreds of images of the moving light to record sharp reflections. Hawkins, T., Einarsson, P., and Debevec, P. 2005, *A dual light stage*, in Proc. EGSR, 91-98 recorded diffuse and specular reflectance behavior of objects with high angular resolution using a surrounding spherical dome and a laser to excite the various surface BRDFs through Helmholtz reciprocity, but achieved limited spatial resolution and required a high-powered laser equipment. Recently, Wang, C.-P., Snavely, N., and Marschner, S. 2011, *Estimating dual-scale properties of glossy surfaces from step-edge lighting*, ACM Trans. Graph. (Proc. SIG-GRAPH Asia) 30, 6 used step-edge illumination to estimate dual scale reflectance properties of highly glossy surfaces, but did not estimate per-pixel BRDFs.

Ma, W.-C., Hawkins, T., Peers, P., Chabert, C.-F., Weiss, M., and Debevec, P. 2007, *Rapid acquisition of specular and diffuse normal maps from polarized spherical gradient illumination*, In Rendering Techniques, 183-194 used spherical gradient illumination representing the 0th and 1st order Spherical Harmonics in an LED sphere to perform view-independent photometric stereo for diffuse and/or specular objects, and used polarization difference imaging to independently model diffuse and specular reflections of faces. Ghosh, A., Chen, T., Peers, P., Wilson, C. A., and Debevec, P. E. 2009, *Estimating specular roughness and anisotropy from second order spherical gradient illumination*, Comput. Graph. Forum 28, 4, 1161-1170 extended this approach by adding 2nd order Spherical Harmonics to estimate spatially varying specular roughness and anisotropy at each pixel. Unfortunately, the use of an LED sphere with limited resolution made the reflectance analysis applicable only to relatively rough specular materials such as human skin, and the use of polarization for component separation becomes complicated for metallic surfaces and near the Brewster angle. To avoid using polarization for reflectance component separation, Lamond, B., Peers, P., Ghosh, A., and Debevec, P. 2009, *Image-based separation of diffuse and specular reflections using environmental structured illumination*, in Proc. IEEE International Conf. Computational Photography modulated gradient illumination patterns with phase-shifted high-frequency patterns to separate diffuse and specular reflections and measure surface normals of 3D objects. The subject technology reformulates and generalizes this frequency-based component separation approach to increasing orders of spherical harmonic illumination. Noting that BRDFs can usefully represented by spherical harmonic functions (e.g. Westin, S. H., Arvo, J. R., and Torrance, K. E. 1992, *Predicting reflectance functions from complex surfaces*, SIGGRAPH Comput. Graph. 26, 2 (Jul.), 255-264), Ghosh, A., Heidrich, W., Achutha, S., and O'Toole, M. 2010, *A basis illumination approach to brdf measurement*, Int. J. Comput. Vision 90, 2 (Nov.), 183-197 used spherical harmonic illumination projected to a zone of a hemisphere for reflectance measurement, but only for single BRDFs from flat samples. Their approach also did not separate diffuse and specular reflectance using the measurements and required very high orders of zonal basis function to record sharp specular reflectance. Instead, in the disclosed work employing up to 5th order spherical harmonics is proposed for both diffuse-specular separation as well as estimating reflectance statistics such as specular roughness and anisotropy.

Highly specular objects have long posed problems for image-based shape reconstruction Blake, A., and Brelstaff, G. 1992, in Physics-Based Vision, Principles and Practice: Shape Recovery, L. B. Wolff, S. A. Shafer, and G. E. Healey, Eds. Jones and Bartlett Publishers, Inc., USA, ch. *Geometry from specularities*, 277-286. Bonfort, T., and Sturm, P. 2003, *Voxel carving for specular surfaces*, In Proc. IEEE International Conference on Computer Vision, 591-596 pro-posed a multi-view voxel carving technique based on reflected observations of a calibrated world pattern, but achieved very low resolution results. Tarini, M., Lensch, H. P., Goesele, M., and Seidel, H.-P. 2005, *3D acquisition of mirroring objects using striped patterns*, Graphical Models 67, 4, 233-259 proposed an alternate shape from distortion approach for high resolution reconstruction. Using a CRT screen as an extended light source, they illuminate a specular object with several stripe patterns to obtain first a matte and then iteratively solve for the depth-normal ambiguity. Chen, T., Goesele, M., and Seidel, H. P. 2006, *Mesostructure from specularities*, in CVPR, 1825-1832 propose measuring mesostructure from specularity using a hand held light source that is waved around while a camera observes the moving specular highlights on the sample to estimate its surface normals. Francken, Y., Cuypers, T., Mertens, T., Gielis, J., and Bekaert, P. 2008, *High quality mesostructure acquisition using specularities*, CVPR, 1-7 propose measuring surface mesostructure instead by using a set of calibrated gray codes projected from an LCD panel in order to localize the surface normal of each surface point. These techniques work well in principle but are limited to scanning small flat objects that are covered by the illumination from an extended source. Adato, Y., Vasilyev, Y., Ben-Shahar, O., and Zickler, T. 2007, *Toward a theory of shape from specular flow*, In Proc. IEEE International Conference on Computer Vision, 1-8 have proposed an alternate approach for shape reconstruction by formulating a set of coupled PDEs based on observed specular flow at a specific surface point. They also derive a simple analytic formulation for a special case of camera rotation about the view axis. While having the advantage of not requiring control over the incident illumination, in practice the method yields only very simple shape reconstructions. In contrast, the disclosed technique combines cues from both diffuse and specular reflectance information to derive high-fidelity geometric models for many common types of objects.

SUMMARY

In one or more aspects of the disclosure, examples are provided for an apparatus to measure surface orientation maps of an object. The apparatus may include a light source configured to illuminate the object with a controllable field of illumination. One or more driver circuits may be configured to drive the light source with modulated signals to generate the controllable field of illumination. A processor may be configured to generate control signals to control the one or more driver circuits to cause the one or more driver circuits to drive the light source with the modulated signals. The controllable field of illumination comprises limited-order Spherical Harmonics (SH) and Fourier Series (FS) illumination patterns with substantially similar polarization, wherein the SH and FS illumination patterns are used with different light sources. The light source may include a plurality of light-emitting elements such as light-emitting diodes (LEDs) mounted on a source assembly, such as an arc-shaped source assembly, which is formed to have a semi-circular arc shape or a polygon arc shape, and can rotate around the object to sweep a partial sphere surface or a full sphere surface around the object. The rotating arc-shaped source assembly can illuminate the object with the SH illumination patterns.

In some implementations, the source assembly further includes a plurality of optical components configured to focus a light-emitting element such as an LED towards a center of the arc-shaped source assembly. The light source may include a linear array of light-emitting elements that is configured to scan the object by moving along an axis substantially perpendicular to the axis of the light source. The driver circuits may be configured to drive each light-emitting element with modulating signals during a scan to create desired planar patterns of illumination. In some aspects, the light source includes a flat panel light source and is configured to display a plurality of frequency patterns. The flat panel light source may be configured to be moved to one or more positions to provide angular illumination over a wide field of view. The flat panel light source may include a video display such as a liquid-crystal display (LCD) or an organic LED (OLED) screen. The flat panel light source can illuminate the object with the FS illumination patterns.

In one or more implementations, the light source includes a closed surface source, such as a dome or a sphere, and can be illuminated with video patterns. The processor may be configured to generate the control signals that include illumination functions that enable the driver circuits to drive the light source to generate the controllable field illumination. The controllable field illumination enables measurement of the reflectance properties of the object, including diffuse and specular albedo, surface orientation, specular roughness, and anisotropy parameters. The controllable field illumination may include a high-resolution continuous spherical lighting condition.

In some other aspects of the disclosure, examples are provided for an apparatus for capturing images of an object to measure reflectance properties of the object. The apparatus may include one or more cameras, each configured to capture at least one image of the object while the object is being illuminated using a controllable field of illumination by a light source. A processor may be configured to process the image(s) of the object captured by each of the cameras. The processor may be configured to process the image(s) by extracting reflectance properties of the object that include one of an albedo, a reflection vector, a roughness, and/or anisotropy parameters of a specular reflectance lobe associated with the object. The processor may be configured to process and extract reflectance properties from one or more images of an object that includes translucent, transparent, and/or reflective surfaces. The processor may employ a multi-view stereo algorithm, which uses specular and diffuse albedo and/or surface orientation measurements for high quality geometry reconstruction.

In some implementations, the processor may be configured to process acquired response to estimate per pixel reflectance parameters for each viewpoint of the object including specular surface normal, specular angle of anisotropy, specular roughness parameters, specular albedo, diffuse albedo, and diffuse normals. The processor may be configured to estimate the specular surface normal by determining a specular reflectance vector by reconstructing a reflectance function using the spherical harmonic basis, and finding a direction vector where the reconstruction attains a maximum value. The spherical harmonic basis may include one of a $3^{rd}$ order, a $4^{th}$ order, a $5^{th}$ order, or a higher order spherical harmonic basis. The spherical harmonic responses may be rotated to align the specular reflection vector to a zonal harmonic axis to produce zonal-aligned spherical harmonic responses.

The specular surface normal may be determined by using the determined specular reflectance vector. The processor may further be configured to rotate the zonal-aligned spherical harmonic responses around the zonal axis by the angle of anisotropy such that the −2 zonal-aligned spherical harmonic response is zero to produce anisotropy-aligned spherical harmonic responses. The specular angle of anisotropy may be determined by finding half of an arctangent of a ratio of the +2 and −2 zonal-aligned spherical harmonic responses, wherein the zonal-aligned spherical harmonic responses comprise one of $3^{rd}$ order, $4^{th}$ order, or $5^{th}$ order zonal-aligned spherical harmonic responses. The specular roughness parameters may be looked up, in a first lookup table, using the ratios computed from the anisotropy-aligned measured spherical harmonic responses. The first lookup table may include a precomputed lookup table of major and minor specular roughness parameters, parameterized by a ratio of $5^{th}$ order to $3^{rd}$ order zonal harmonic response, and the ratio of +2 and zonal harmonic response, using synthetic rendering with a specular model of choice, and wherein the +2 and zonal harmonic response comprises one of $3^{rd}$, $4^{th}$, $5^{th}$ order, or higher order +2 and zonal harmonic response.

The processor may further be configured to estimate the specular albedo by looking up a nominal zonal harmonic in a second lookup table using the major and minor specular roughness parameters. The second lookup table may include a precomputed lookup table of zonal harmonic responses with unit specular albedo. The specular albedo may be found as a ratio of the $3^{rd}$ order anisotropy-aligned measured spherical harmonic response to the nominal response from the second lookup table. The nominal zonal harmonic may include a zonal aligned response or one of $3^{rd}$, $4^{th}$, $5^{th}$ order, or higher order nominal zonal harmonic. The processor may further be configured to synthesize, by rendering or a lookup table, a set of specular-only spherical harmonic responses using the specular normal, the specular angle of anisotropy, the specular roughness parameters, and specular albedo. A set of diffuse-only spherical harmonic responses may be determined by subtracting the specular-only spherical harmonic responses from measured responses. A diffuse albedo may be determined as a product of a $0^{th}$ order diffuse-only spherical harmonic response and a normalizing constant (e.g., $2/\sqrt{\pi}$). A diffuse normal may be determined as a vector with X, Y, and Z components equal to the −1, 0, and +1 responses of $1^{st}$ order diffuse-only spherical harmonic responses, normalized to a unit vector.

In some other aspects of the disclosure, examples are provided for an apparatus for scanning an object to measure reflectance properties of the object. The apparatus may include a light source that is configured to illuminate the object with a controllable field of illumination including a series of different frequencies of illumination. One or more cameras may be configured to capture image(s) of the object. A processor maybe configured to process the image(s) to extract the reflectance properties of the object. The processor may extract reflectance properties of the object including an albedo, a reflection vector, a roughness, and/or anisotropy parameters of a specular reflectance lobe associated with the object. The controllable field of illumination comprises limited-order Spherical Harmonics (SH) and Fourier Series (FS) illumination patterns, which are used with different light sources. Each of the cameras are calibrated using a single-shot camera calibration process including using a checkboard cylinder.

In some other aspects of the disclosure, examples are provided for a method for determining the reflectance properties of an object. The method may include Illuminating the object with a plurality of lighting conditions including a series of different frequencies of illumination, digitally photographing the object under the plurality of lighting conditions, and analyzing digital photographs of the object taken under the plurality of lighting conditions to determine diffuse, specular, and specular roughness values at each surface point of the object. The method may further include creating the plurality of lighting conditions by one of: sweeping an array of light sources across an area including the object, modulating light intensities of light-emitting elements of an array of light-emitting elements to produce the plurality of lighting conditions, or using a flat panel light source comprising a video display such as a liquid-crystal display (LCD) or an organic LED (OLED) screen. The flat panel light source can be moved to one or more positions to provide angular illumination over a wide field of view. The flat panel source can illuminate the object with the FS illumination patterns.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 2A illustrates an example of a system for measuring reflectance properties of an object, in accordance with some implementations.

FIG. 2B illustrates examples of an exposure of an object and the object lit by a sphere of light, in accordance with some implementations.

FIG. 2C illustrates examples of a cross-sectional view of a light source and plots of corresponding vertical intensity profiles, in accordance with some implementations.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
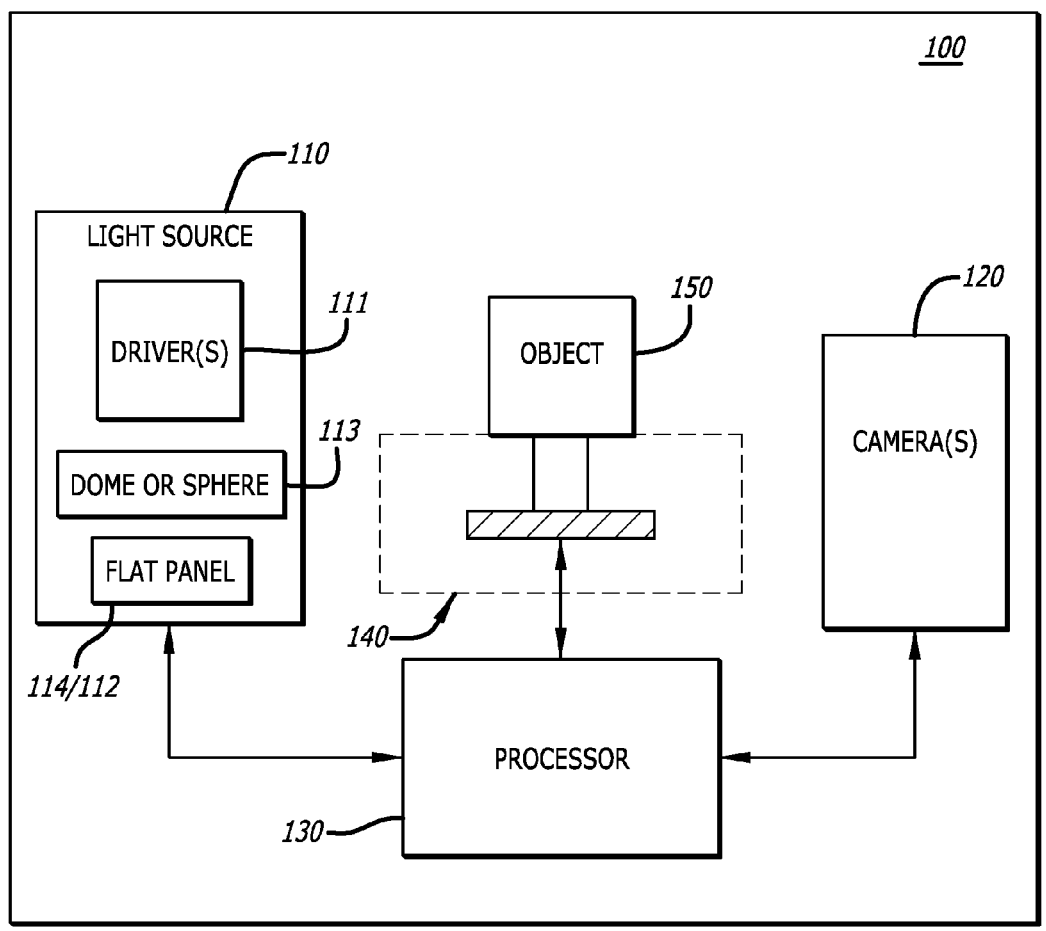
FIG. 1 is a conceptual diagram illustrating an example of a system for measuring reflectance properties of an object in accordance with some implementations.

FIG. 1 is a conceptual diagram illustrating an example of a system 100 for measuring reflectance properties of an object in accordance with some implementations of the subject technology. The system 100 includes a light source 110, one or more cameras 120, a processor 130, and a platform 140, on which an object 150 can be placed. The light source 110 can illuminate the object 150 (e.g., a specular object) with a controllable field of illumination using limited-order (e.g., up to $5^{th}$ order) Spherical Harmonics (SH) or Fourier Series (FS) illumination patterns. The light source 110 may include one or more driver circuits 111 that can drive the light source with modulated signals to generate the controllable field of illumination. The control signals may be generated by the processor 130 or one or more other processors. The cameras 120 can capture one or more images of the object 150 while the object 150 is being illuminated by the controllable field of illumination of the light source 110. The platform 140 can rotate the object with various rotation angle steps to allow the object 150 to be seen by the cameras 120 at desired angles. The processor can process the images of the object to extract reflectance properties of the object including an albedo, a reflection vector, a roughness, or anisotropy parameters of a specular reflectance lobe associated with the object 150, and/or other specular and/or diffuse parameters of the object 150. The subject technology can minimize the number of required images and maximizes image contrast due to absence of inter-reflections.

In one or more implementations, the light source 110 may include a source assembly, such as an arc-shaped source assembly formed to have a semi-circular or polygon arc shape. The arc-shaped source assembly may include multiple light emitting elements such as light-emitting diodes (LEDs) and a number of optical components (e.g., optical lenses) that can focus the light-emitting elements towards a center of the arc-shaped source assembly, as descried in more details herein. The source assembly can rotate around the object 150 to sweep a partial sphere surface or a full sphere surface around the object 150. The driver circuits can perform fine-grained intensity control over the LED-based lighting to enable image-based lighting of the object 150 with very high resolution (e.g., 105×360) HDR lighting environment.

To digitize the reflectance properties of flat material samples (e.g., leather, cloth, car paint, brushed and/or stamped metal) one can create a planar variant of the source assembly. In this configuration, the material is placed face-up on a horizontal surface, with one or more cameras aimed down framed on the sample. For these applications, the light source 110 may include a linear array of light-emitting elements, such as LEDs that is configured to scan the object by moving along an axis perpendicular to the axis of the linear array light source. During a scan, the LEDs may be driven by the driver circuits with modulating signals to create desired planar patterns of illumination.

For example, the light source can be 60 cm long, oriented along the north-south axis, and held 10 cm above a 20 cm×20 cm material sample. The light source can be translated along the east-west direction plus or minus 30 cm from the center of the sample, and illuminate the sample over the majority of its upper hemisphere of incident lighting directions. Unlike some existing linear light source reflectometry approaches, the cameras 120 may expose a corresponding digital image sensor for the entire travel time of the light source across the sample, allowing the effect of planar light patterns to be generated. Since each of the LEDs can be modulated individually during the motion, planar patterns of illumination can be created.

The equivalent of the Spherical Harmonic patterns that may be used is, of course, the Fourier series built from sine and/or cosine waves with increasing frequency. Analogous processes may be performed for separating diffuse and specular reflection and for estimating surface orientations based on the predicted maximum response to the frequency illumination. The breadths and orientation of a potentially anisotropic specular lobe can be estimated by using analogous mathematics. Multiple cameras (e.g., using shift lenses to keep the flat subject in sharp focus from different vantage points) may be used to "see around" the arm's occlusion of the sample.

In some aspects, the light source 110 may include a flat panel light source that can display multiple frequency patterns. The flat panel light source 114 may be arranged to be moved to one or more (e.g., five or more) positions to provide angular illumination over a wide field of view (e.g., 360 degrees). Examples of the flat panel light source may include a video display 112 such as a liquid-crystal display (LCD), an organic LED (OLED) screen, or other flat panel displays.

In one or more implementations, the light source 110 may be in the form of a closed surface such as a dome, a sphere 113, or any other closed surface. For example, the object 150 may be illuminated with the requisite continuous angularly varying illumination patterns using video projection techniques. For example, the subject may be placed inside the closed surface, and video can be projected from one or more video projectors to cover the inside of the sphere with video patterns. Calibration may be necessary to make sure that the projects blend together at the seams and that each addresses the appropriate region of the sphere. A video monitor such as an LCD panel or an OLED screen displaying the frequency patterns could also be moved to one or more positions to provide angular illumination over a wide field of view. The closed surface can also be projected from the outside if it is translucent to some degree. The processor 130 may computationally compensate for the inter-reflected light within the sphere in this case. The images can be optically integrated through long-exposure photography or shot as single images and added together computationally as a pre-process. The applied techniques may benefit from the use of high dynamic range imaging techniques.

FIG. 2A illustrates an examples of a system 200A for measuring reflectance properties of an object, in accordance with implementations of the subject technology. The system 200A includes a source assembly (e.g., an LED arm) 210 that can illuminate an object 250 placed on a platform (e.g., a turntable) 240 with any series of continuous spherical incident illumination conditions. One or more cameras (e.g., 5) 220 can take photographs of the object as it is illuminated by the source assembly 210. The source assembly 210 can be 1 m diameter semi-circular arc of a number of (e.g., 105) light-emitting elements such as LEDs (e.g., white LEDS), which can rotate about its central vertical axis using a motion control motor.

The object 250 to be scanned sits on the platform 240 at the center of the arc of the source assembly 210. The platform 240 is motorized to rotate around the vertical axis yielding additional views of the object. In some implementations, the object is rotated to eight positions, 45 degrees apart. In some aspects, the platform is a dark cylinder which can light up from light-emitting elements mounted inside it; this version can measure an additional transparency map for objects such as eyeglasses.

The cameras 220 include an array of a number of (e.g., 5) cameras (e.g., machine vision cameras) arranged, for example, in a plus sign configuration, with each camera being spaced apart (e.g., about fifteen degrees) from its neighbor(s). Each camera has a narrow field of view lens framed and focused on the object.

The source assembly 210 may spin, for example, at one revolution per second during which the intensities of the light-emitting elements are modulated to trace out arbitrary spherical illumination environments. Differences in LED intensity due to manufacturing are compensated for by calibrating the intensity of LEDs.

FIG. 2B illustrates examples of a cross-sectional view 200B of a light source and plots of corresponding vertical intensity profiles, in accordance with implementations of the subject technology. As seen in cross-sectional view 200B, each LED 270 is focused toward the center with an optical element 272 (e.g. a clear plastic optical element) which is aimed through two spaced apart layers of diffusion (e.g., diffusers 1 and 2). The diffusion allows the light-emitting elements s 270 to form a smooth arc of light when they are all on, but baffles (e.g., occludors) 274 between the optic elements 272 help each light-emitting element 270 to have only a local effect on the light assembly 210, as seen in the graphs 276 and 278.

Since the light assembly 210 spins through the space more slowly near its top and bottom than at the equator, it would naturally produce more light per solid angle near the poles than from the equator. To counteract this, a curved aperture slit is applied to the light assembly 210, which is 1 cm wide at the equator and tapers toward 0 cm wide at the poles proportional to the cosine of the angle to the center.

FIG. 2C illustrates examples of an exposure of an object and the object lit by a sphere of light, in accordance with implementations of the subject technology. The differences in LED intensity due to manufacturing may be compensated by calibrating the intensity of each LED as reflected in a chrome ball placed in the center of the system 200A of FIG. 2A. For example, Pulse width modulation may be used to achieve 256 levels of intensity with 400 divisions around the equator, allowing a resolution of 400×105 pixel lighting environment to be produced. For the exposure 260, each camera is exposed for the full second of each rotation to record a full sphere of incident illumination as the source assembly rotates.

Additionally, a one-rotation pass may be performed where the object is only illuminated from the back and dark on the front in order to obtain masks for visual hull for subsequent stereo processing. The use of a spinning arm, as the lighting assembly 210 of FIG. 2A, largely eliminates problematic interreflections, which would occur if one were to surround the object with a projection surface. The applied spherical lighting patterns minimize the brightness disparity between diffuse and specular reflections, as compared to techniques with more concentrated illumination sources, in which a perfectly specular sphere and perfectly diffuse sphere of the same albedo appear the same brightness under uniform light. Nonetheless, to optimally estimate reflectance properties of both high albedo and low albedo surfaces with low noise, high dynamic range photography, for example, with 3 exposures per lighting condition and one and a half stops apart may be employed.

The motion of the arc creates a vertical sliver of reflection occlusion when it passes in front of each camera (see the dark line down the center of the sphere in 262). In processing, this missing reflectance information can be estimated from data in the neighboring views. In some aspects, datasets can be captured in approximately ten minutes.

Figure 3A:
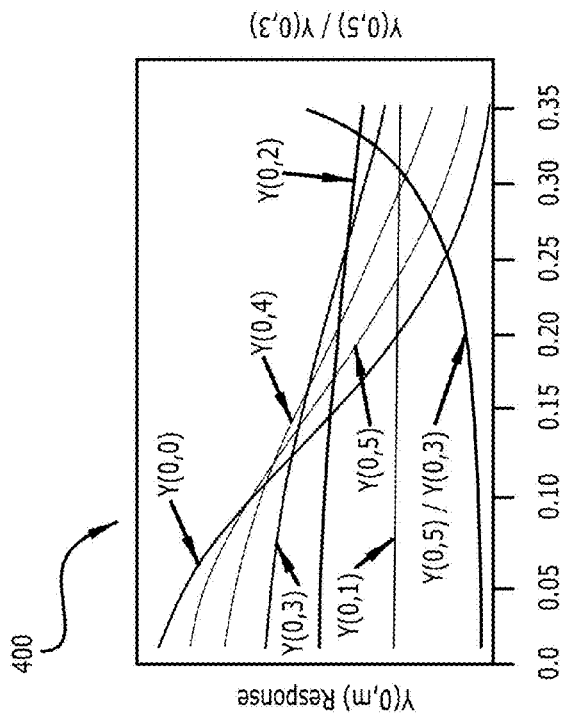
FIGS. 3A and 3B illustrate examples of Spherical Harmonic (SH) functions up to $3^{rd}$ order and responses of diffused, specular, and diffused-plus-specular reflectance lobes to the first six zonal harmonics.
Figure 3B:
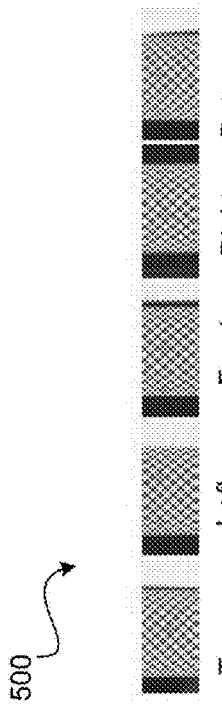

FIGS. 3A and 3B illustrate examples of Spherical Harmonic functions 330A up to $3^{rd}$ order and responses 300B of diffused, specular, and diffused-plus-specular reflectance lobes to the first six zonal harmonics. The subject technique uses an algorithm to estimate per-pixel reflectance parameters for a single viewpoint of an object (e.g., 250 of FIG. 2A) observed under SH illumination functions $y_l^m(\omega))=y_l^m$ (x; y; z) up to, for example, 5th order where ω is the unit vector (x; y; z), as shown in FIG. 3A. In some aspects, a reflectance model consisting of a Lambertian diffuse lobe D and a specular lobe S with roughness and anisotropy may be applied. Holding the view vector fixed, the reflectance functions D(ω) and S(ω) can be parameterized by the unit vector ω indicating the incident illumination direction. Of course, D(ω) and S(ω) are not observed directly, but rather the responses of their sum f(ω)=D(ω)+S(ω) to the SH illumination functions are observed, which are denoted by:

$$f_l^m = \int f(\omega) y_l^m(\omega) d\omega.$$

A key to the disclosed reflectometry technique is the prior observation that a Lambertian diffuse lobe exhibits the vast majority of its energy in only the 0th, 1st, and $2^{nd}$ order Spherical Harmonic bands. It is observed that this implies that the 3rd order SH coefficients and above respond only to the specular lobe S(ω), so that $S_l^m \sim f_l^m$ for $l \geq 3$, as seen in FIG. 3B. Subsequently, the specular lobe's albedo, reflection vector, roughness, and anisotropy parameters are estimated from the higher order responses by comparing to the higher-order responses of lobes from a reflectance model. From the specular reflectance parameters, the responses $S_0^0$ and $S_l^m$ of the specular lobe to the lower order harmonics can be estimated and subtracted from the observations to estimate the response of just the diffuse lobe D(ω) to the $0^{th}$ and 1st order harmonics $D_0^0$, $D_l^m$. From these response, the diffuse albedo and diffuse surface normal can be estimated, yielding a complete model of diffuse and specular reflectance per pixel from a small number of observations.

The disclosed acquisition system (e.g., 200A of FIG. 2A) can acquire the responses of the object (e.g., 250 of FIG. 2A) to the thirty-six SH illumination conditions up to the 5th order. Since the system cannot produce negative light, the SH functions above 0th order are offset and scaled to produce two lighting patterns, one with pixel values between 0 and 255 and a complementary condition with pixel values from 255 to 0. The difference of these two images yields the response to the Spherical Harmonics. In some aspects, fewer images could be acquired by using the harmonics scaled 0 to 255, but the disclosed approach distributes camera noise more evenly through the range of intensities.

Figure 4:
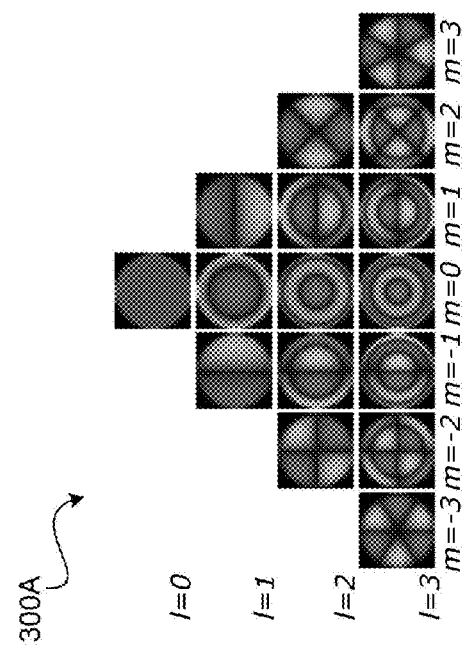
FIG. 4 illustrates examples of plots of the responses of an isotropic specular lobe to the first six zonal harmonic.

FIG. 4 illustrates examples of plots 400 of the responses y(0,0), y(0,1), y(0,2), y(0,3), y(0,4), y(0,5), and y(0,5)/y(0,3) of an isotropic specular lobe to the first six zonal harmonics. In one or more implementations, the response of the chosen reflectance model's specular lobe to the SH illumination basis over its range of valid roughness values are computed and shown versus anisotropic roughness parameter α. For example, an arbitrarily model for specular lobe $f_{a1,a2}^s$ is chosen and anisotropic roughness parameters $a_1 \geq a_2$ ranging from 0 (perfectly sharp) to 0.35 (very rough) in increments of 0.05 are chosen. The surface at normal incidence along the z-axis is viewed, a unit specular albedo $\rho_s=1$ is chosen, and the axis of anisotropy is aligned to 0 degrees along the x-axis. The lobes are then numerically integrated against the SH basis to determine coefficient table $Rl_l^m (a_1, a_2)$ for each order l across the range of α. The responses shown in FIG. 4 correspond to values of responses $Rl_l^0 (a, a)$ of an isotropic specular lobe to the first six zonal harmonics $y_l^0$ as the roughness increases from $a_1=0$ to $a_1=0.35$. The dotted line shows the ratio $Rl_3^0/Rl_5^0$ which is used to determine specular roughness.

The response of the lobes to the SH basis has useful properties for reflectance measurement. Since isotropic lobes are radially symmetric, only the zonal SH basis functions $y_l^0$ yield a nonzero response when $a_1=a_2$. Even when the lobe is anisotropic, it is symmetrical across both the x and y axes in that $f_{a1,a2}^s(x, y, z) z)=f_{a1,a2}^s(\pm x, \pm y)$ so its response to the basis functions $y_l^{\pm 1}$ (for $l \geq 1$) are both zero.

Figure 5:
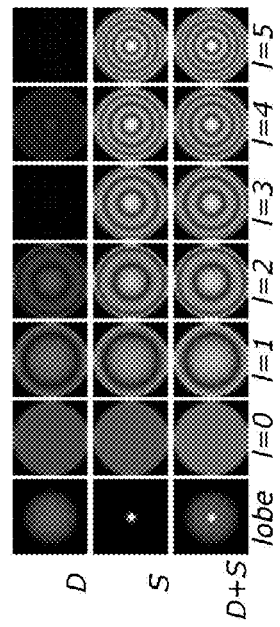
FIG. 5 illustrates examples of views of a calibration cylinder, in accordance with some implementations.

FIG. 5 illustrates examples of views of a calibration cylinder 500, in accordance with implementations of the subject technology. The checkerboad cylinder 500 (e.g., having a 15 cm diameter) can be sued to calibrate the cameras (e.g., 220 of FIG. 2A) using a single-shot camera calibration process. In some implementations, the checkerboad cylinder 500 has three colored dots to consistently identify the cylinder's orientation in each view. The checker size provides a known distance to establish scale. The checker corners are detected using a corner detector and refined to subpixel coordinates. The pixel coordinates of the detected corners are matched to the corresponding 3-D points on an ideal cylinder.

The views in FIG. 5 include top, left, front, right, and bottom views of the calibration cylinder from the camera array 220. Initial estimates can be provided of the camera poses and focal lengths to a least squares of the distance between the detected corner points and their 3D reprojections in the five camera models. First, only the cameras' extrinsic parameters are optimized, and then the cameras' intrinsic (including two terms of radial distortion) are optimized, and finally the 3D positions of the points on the cylinder are optimized so that it need not be constructed with great precision. The solver converges in about one minute yielding average point re-projection errors of 0.15 to 0.35 pixels.

Figure 6:
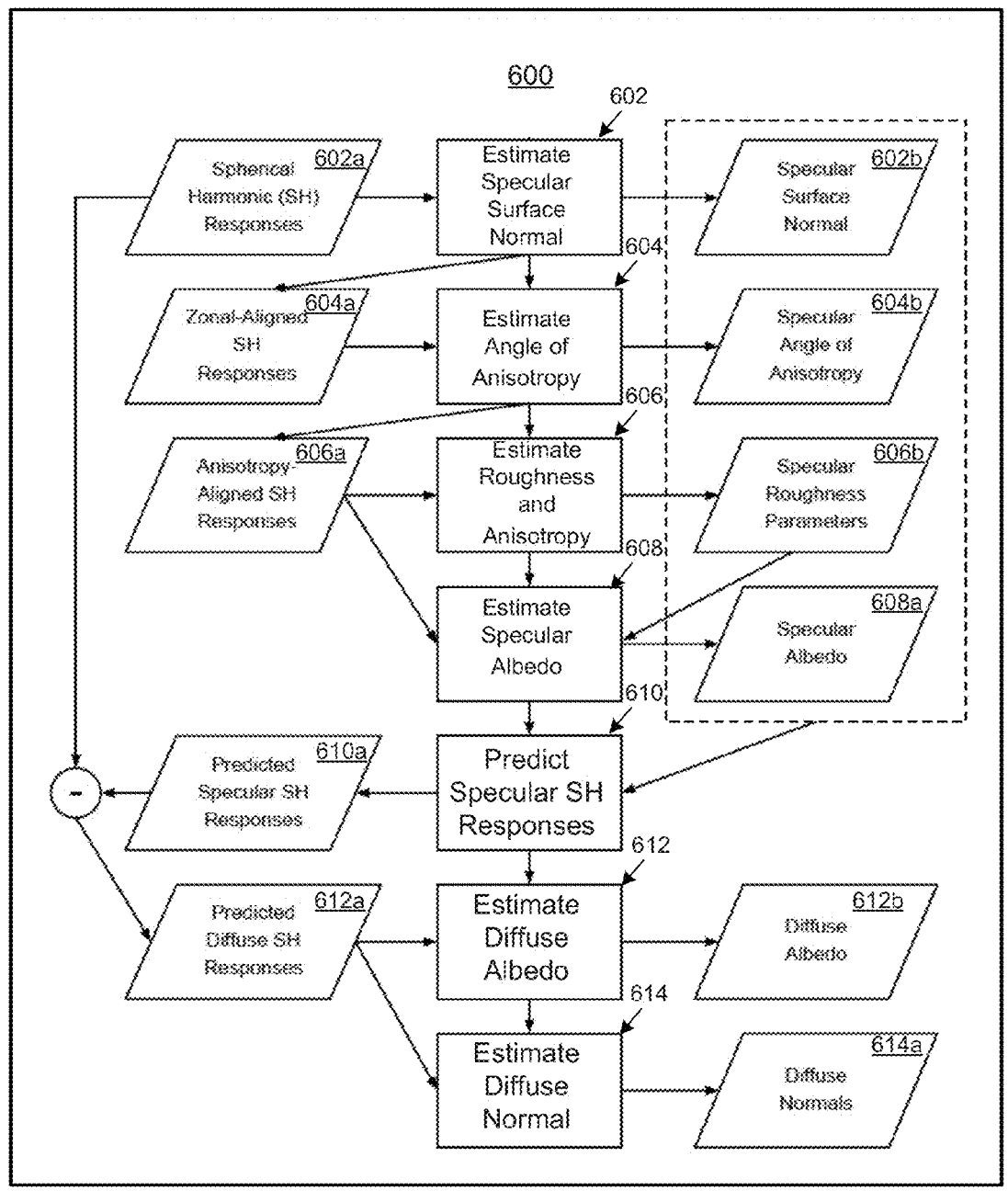
FIG. 6 illustrates an example of a method for extracting reflectance properties of an object, in accordance with some implementations.

FIG. 6 illustrates an example of a method 600 for extracting reflectance properties of an object, in accordance with implementations of the subject technology. At operation block 602, the specular reflection vector (e.g., specular surface normal 602b) may be found by reconstructing the reflectance function using Spherical Harmonic (SH) responses 602a (e.g., only the $3^{rd}$ order SH basis), and finding the direction vector where the reconstruction attains its maximum. The Spherical Harmonic responses can then be rotated such that the specular reflection vector is aligned to the zonal harmonic axis, producing the "zonal-aligned" Spherical Harmonic responses 604a. In some embodiments, somewhat higher orders such as $4^{th}$ order or $5^{th}$ order or higher could be used.

At operation block 604, the specular angle of anisotropy 604b is estimated. The specular angle of anisotropy is half the arctangent of the ratio of the +2 and −2 zonal-aligned $3^{rd}$ order Spherical Harmonic responses. The zonal-aligned Spherical Harmonic responses 604a are then rotated around the zonal axis by the angle of anisotropy such that the −2 zonal-aligned $3^{rd}$ order Spherical Harmonic responses is zero, producing the "anisotropy-aligned" Spherical Harmonic responses. In some embodiments, somewhat higher orders such as $4^{th}$ order or $5^{th}$ order or higher could be used.

At operation block 606, anisotropy aligned SH responses 606a are used to estimate the specular roughness parameters 606b. This step may make use of a precomputed lookup table of the major and minor specular roughness parameters, parameterized by the ratio of $5^{th}$ order to $3^{rd}$ order zonal harmonic response, and the ratio of $3^{rd}$ order +2 and $3^{rd}$ order zonal harmonic response, using synthetic rendering with a specular model of choice. The specular roughness parameters can be looked up in the table using the same ratios computed from the anisotropy-aligned measured Spherical Harmonic responses. In some embodiments, ratios using other orders such as $4^{th}$ order or $5^{th}$ order or higher could be used.

At operation block 608, anisotropy aligned SH responses 606a and the specular roughness parameters 606b are used to estimate specular albedo 608a. This step can make use of a precomputed lookup table of zonal harmonic responses assuming unit specular albedo. The nominal $3^{rd}$ order zonal harmonic can be looked up in the table using the specular roughness parameters 606b. The specular albedo is the ratio of the $3^{rd}$ order anisotropy-aligned measured Spherical Harmonic response to the nominal response from the table. In some embodiments, the zonal-aligned response may be used, and/or somewhat higher orders such as $4^{th}$ order or $5^{th}$ order or higher could be used.

At operation block 610, using the specular normal 602b, specular angle of anisotropy 604b, specular roughness parameters 606b, and specular albedo 608a, a set of specular-only SH responses 610a are synthesized using synthetic rendering or a lookup table. A set of diffuse-only Spherical Harmonic responses 612a are computed by subtracting the specular-only responses from the measured responses.

At operation block 612, the diffuse albedo 612b is estimated using the predicted diffuse SH response 612a. The diffuse albedo is the $0^{th}$ order diffuse-only Spherical Harmonic response 612a times a normalizing constant (e.g., $2/\sqrt{\pi}$).

At operation block 614, the diffuse normal 614a is computed as the vector with X, Y, and Z components equal to the −1, 0, and +1 responses of the $1^{st}$ order diffuse-only Spherical Harmonic responses, normalized to a unit vector.

The steps of the method 600 can be implemented by the processor 130 of FIG. 1 or any other processor.

Figure 7:
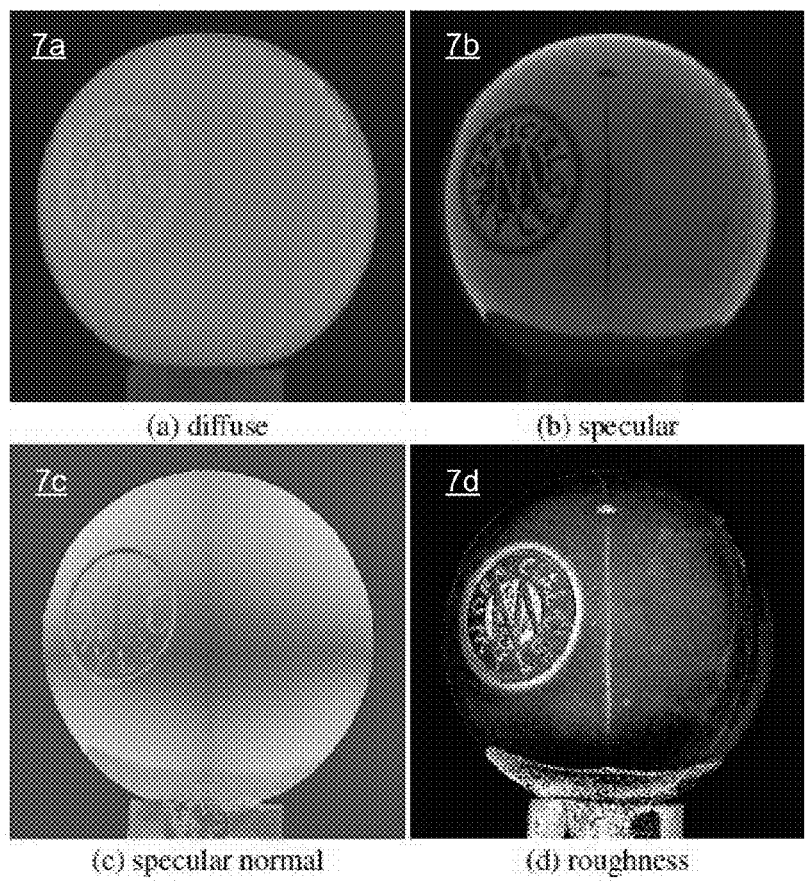
FIG. 7 illustrates examples of estimated reflectance maps of a plastic ball, in accordance with some implementations.

FIG. 7 illustrates examples of estimated reflectance maps 7a-7d of a plastic ball, in accordance with implementations of the subject technology. The maps 7a-7d are recovered maps for a shiny plastic ball 262 of FIG. 2C under uniform illumination. The maps 7a-7d show good diffuse/specular separation and the normals trace out the spherical shape, except in areas of reflection occlusion near the bottom. The roughness is low and consistent across the ball, but becomes especially low around the periphery presumably due to Fresnel gain, which can be observed in the specular map.

Figure 8:
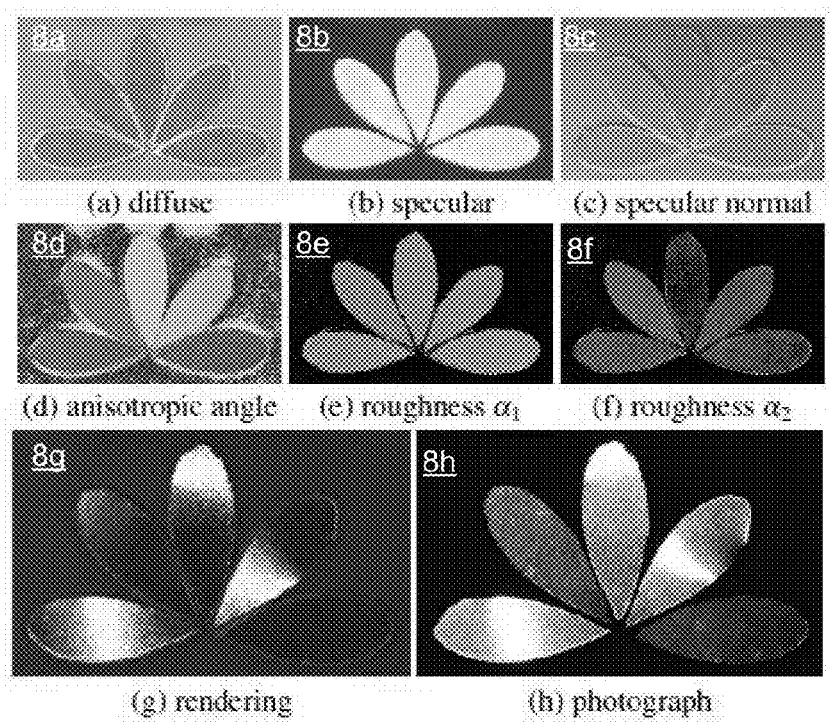
FIG. 8 illustrates examples of maps, a rendering, and a photo of a brushed metal object, in accordance with some implementations.

FIG. 8 illustrates examples of maps 8a-8f, a rendering 8g, and a photograph 8h of a brushed metal object, in accordance with implementations of the subject technology. The maps 8a-8f are recovered for an arrangement of five slightly bent anisotropic brushed metal petals at different angles. The maps exhibit four different angles of anisotropy. The major-axis roughness $\alpha 1$ is consistent for all five petals, and the minor-axis roughness $\alpha 2$ is sharper overall but especially low for the vertical petal. It is understood that this inconsistency is due to the LED arm's higher resolution and lack of blur around the equator compared to along the length of the arm. The rendering 8g and the validation photograph 8h, both under point-source illumination, are still reasonably consistent, though the tails of the specular lobes are wider in the photograph. This is likely because of the tendency of the applied model lobe to fall to zero too quickly. A different reflectance model might better represent this reflectance.

Figure 9:
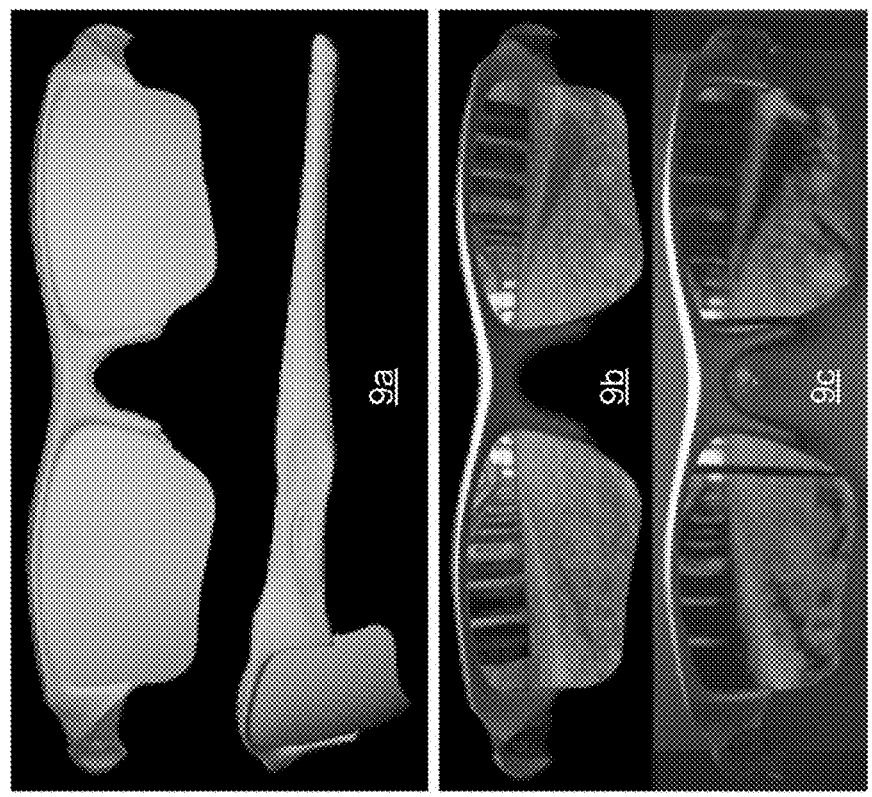
FIG. 9 illustrates examples of views of a 3D geometry, a validation rendering, and a photograph with environmental illumination of a sunglass, in accordance with some implementations.

FIG. 9 illustrates examples of views of a 3D geometry 9a, a validation rendering 9b, and a photograph with environmental illumination 9c of a sunglass, in accordance with implementations of the subject technology. The scanning process for a pair of sunglasses with several materials of varying roughness on the frames and strongly hued lenses with a mirror-like reflection are shown in FIG. 9. The reflectance maps correctly show very little diffuse reflection on the lenses and spatially varying roughness on the ear pieces. The glasses were scanned in five poses for twenty-five viewpoints total. The diffuse and specular albedo and diffuse and specular normals were used in the multiview shape reconstruction shown in FIG. 9 providing merged maps in a cylindrical texture space from all 25 views. The geometry success fully reconstructs both the diffuse ear pieces and the mirror-like lenses in a single process. FIG. 9 also provides a ground truth comparison of the rendered glasses (e.g., 9b) to the real pair of glasses lit by environmental illumination (e.g., 9h).

Figure 10:
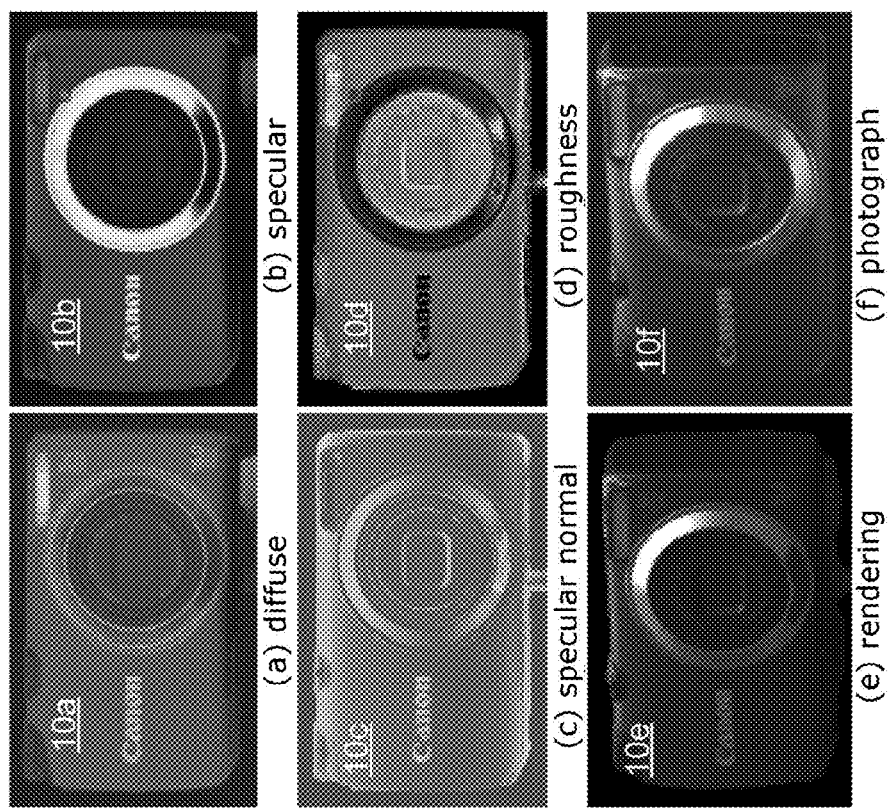
FIG. 10 illustrates examples of reflectance maps of a 3D model, a rendering, and a photograph with environmental illumination of a digital camera, in accordance with some implementations.

FIG. 10 illustrates examples of reflectance maps 10a-10d of a 3D model, a rendering 10e, and a photograph with environmental illumination 10f of a digital camera, in accordance with implementations of the subject technology. The maps 10a-10d and the geometry shown in FIG. 10 are for a digital camera with several different colors and roughnesses of metal and plastic and an anisotropic brushed metal bezel around the lens. The maps 10a-10d success fully differentiate the materials and allow the renderings (e.g., 10e) to give a faithful impression of the original device as shown in the photograph 10f.

The subject technology presents a novel technique for acquiring the geometry and spatially-varying reflectance properties of 3D objects (e.g., objects of FIGS. 9 and 10) by observing them under continuous Spherical Harmonic illumination conditions. The technique is general enough to characterize either entirely specular or entirely diffuse materials, or any varying combination across the surface of the object. In some aspects, the technique employs a novel computational illumination setup including a rotating arc of controllable LEDs which sweep out programmable spheres of incident illumination during 1-second exposures (e.g., 200A of FIG. 2A). The object is illuminated with a succession of Spherical Harmonic illumination conditions, as well as photographed environmental lighting for validation. From the response of the object to the harmonics, diffuse and specular reflections are separated, world-space diffuse and specular normals are estimated, and anisotropic roughness parameters for each view of the object are computed. The maps of both diffuse and specular reflectance are then used to form correspondences in a multiview stereo algorithm, which allows even highly specular surfaces to be corresponded across views. The algorithm yields a complete 3D model and a set of merged reflectance maps. In one or more aspects, this technique is used to digitize the shape and reflectance of a variety of objects difficult to acquire with other techniques and present validation renderings which match well to photographs in similar lighting. More detailed description of the subject techniques and algorithms and the results can be found in "Acquiring reflectance and shape from continuous Spherical Harmonic illumination," by Borom Tunwattanapong, Graham Fyffe, Paul Graham, Jay Busch, Xueming Yu, Abhijeet Ghosh, and Paul Debevec, published in ACM Trans. Graph. 32, 4, Article 109 (Jul. 2013), which is incorporated by reference herein in its entirety.

Figure 11:
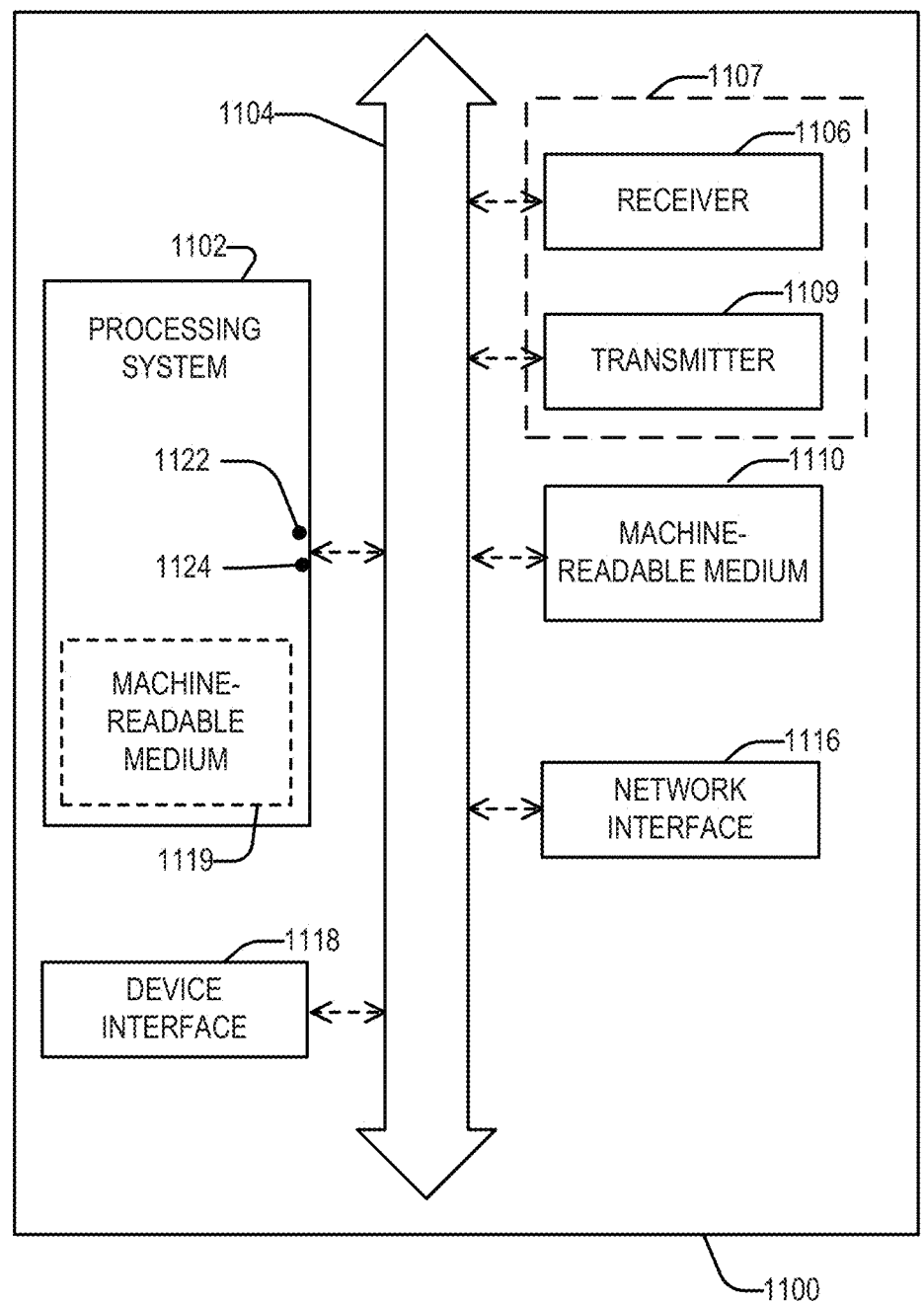
FIG. 11 illustrates an example of a computer system for implementing some aspects of the subject technology.

FIG. 11 illustrates an example of a computer system 1100 for implementing some aspects of the subject technology. Examples of the system 1100 may include a server, a personal computer, a laptop computer, a tablet, or a handheld communication device. The system 1100 includes a processing system 1102, which may include one or more processors or one or more processing systems. A processor can be one or more processors. The processing system 1102 is capable of communication with a receiver 1106 and a transmitter 1109 through a bus 1104 or other structures or devices. In some aspects, processing system 1102 may generate audio, video, multimedia, and/or other types of data to be provided to the transmitter 1109 for communication. In addition, audio, video, multimedia, and/or other types of data can be received at the receiver 1106, and processed by the processing system 1102.

The processing system 1102 may include a general-purpose processor or a specific-purpose processor for executing instructions and may further include a machine-readable medium 1119, such as a volatile or non-volatile memory, for storing data and/or instructions for software programs. The instructions, which may be stored in a machine-readable medium 1110 and/or 1119, may be executed by the processing system 1102 to control and manage access to the various networks, as well as provide other communication and processing functions. The instructions may also include instructions executed by the processing system 1102 for various user interface devices, such as a display 1112 and a keypad 1114. The processing system 1102 may include an input port 1122 and an output port 1124. Each of the input port 1122 and the output port 1124 may include one or more ports. The input port 1122 and the output port 1124 may be the same port (e.g., a bi-directional port) or may be different ports.

The processing system 1102 may be implemented using software, hardware, or a combination of both. By way of example, the processing system 1102 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 1119) may include storage integrated into a processing system such as might be the case with an ASIC. Machine-readable media (e.g., 1110) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 1102. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. Instructions may be executable, for example, by the processing system 1102 or one or more processors. Instructions can be, for example, a computer program including code.

A network interface 1116 may be any type of interface to a network (e.g., an Internet network interface), and may reside between any of the components shown in FIG. 11.

A device interface 1118 may be any type of interface to a device and may reside between any of the components shown in FIG. 11. A device interface 1118 may, for example, be an interface to an external device (e.g., USB device) that plugs into a port (e.g., USB port) of the system 1100.

A transceiver block 1107 may represent one or more transceivers, and each transceiver may include a receiver 1106 and a transmitter 1109. A functionality implemented in a processing system 1102 may be implemented in a portion of a receiver 1106, a portion of a transmitter 1109, a portion of a machine-readable medium 1110, a portion of a display 1112, a portion of a keypad 1114, or a portion of an interface 1116, and vice versa.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

One or more of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-ROW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Unless otherwise indicated, the methods, algorithms, and process that have been discussed herein can be implemented with the computer system 1100 configured to perform the functions that have been described herein for the component.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. An apparatus to measure surface orientation maps of an object, the apparatus comprising:
 a light source configured to illuminate the object with a controllable field of illumination;
 one or more driver circuits configured to drive the light source with modulated signals to generate the controllable field of illumination; and
 a processor configured to generate control signals to control the one or more driver circuits to cause the one or more driver circuits to drive the light source with the modulated signals,
 wherein the controllable field of illumination comprises limited-order spherical Harmonics (SH) or Fourier Series (FS) illumination patterns, wherein different light sources produce the SH illumination patterns and the FS illumination patterns.

2. The apparatus of claim 1, wherein the light source comprises a linear array of LEDs that is configured to scan the object by moving along an axis perpendicular to an axis of the light source, wherein the one or more driver circuits are configured to drive each LED with modulating signals during a scan to create desired planar patterns of illumination.

3. The apparatus of claim 1, wherein:
 the light source comprises a flat panel light source and is configured to display a plurality of frequency patterns,
 the flat panel light source is configured to be moved to one or more positions to provide angular illumination over a wide field of view,
 the flat panel light source comprises a video display, and

19 the flat panel light source is configured to illuminate the object with the FS illumination patterns.

4. The apparatus of claim 1, wherein:
the light source comprises a closed surface source,
the closed surface source comprises a dome or a sphere, and
the closed surface source is illuminated with video patterns.

5. The apparatus of claim 1, wherein:
the processor is configured to generate the control signals that comprise illumination functions that enable the one or more driver circuits to drive the light source to generate the controllable field illumination,
the controllable field illumination enables measurement of reflectance properties of the object comprising one or more of diffuse albedo, specular albedo, surface orientation, specular roughness, and anisotropy parameters,
the controllable field illumination comprises a high-resolution continuous spherical lighting condition, and
the limited-order SH comprises up to fifth order SH.

6. The apparatus of claim 1, wherein:
the light source comprises a plurality of light-emitting elements including light-emitting diodes (LEDs),
the plurality of light-emitting elements are mounted on a source assembly,
the source assembly comprises an arc-shaped source assembly, and
the arc-shaped source assembly is formed to have a semi-circular arc shape or a polygon arc shape,
the source assembly is configured to rotate around the object,
the source assembly is configured to rotate around the object to sweep a partial sphere surface or a full sphere surface around the object, and
the rotating arc-shaped source assembly is configured to illuminate the object with the SH illumination patterns.

7. The apparatus of claim 6, wherein the source assembly further comprises a plurality of optical components, and wherein each optical component is configured to focus an LED towards a center of the arc-shaped source assembly.

8. An apparatus for capturing images of an object to measure reflectance properties of the object, the apparatus comprising:
one or more cameras, each camera configured to capture at least one image of the object while the object is being illuminated using a controllable field of illumination with a series of different frequencies by a light source; and
a processor configured to process the at least one image of the object captured by each of the one or more cameras,
wherein the processor is configured to process the at least one image of the object by extracting reflectance properties of the object including at least one of an albedo, a reflection vector, a roughness, and anisotropy parameters of a specular reflectance lobe associated with the object,
wherein the controllable field of illumination comprises limited-order Spherical Harmonics (SH) or Fourier Series (FS) illumination patterns, wherein different light sources produce the SH illumination patterns and the FS illumination patterns, and wherein the one or more cameras are configured to acquire responses of the object to illumination conditions of at least the $3^{rd}$ order, and wherein the processor is configured to process the acquired responses to estimate per pixel reflectance parameters for each viewpoint of the object

20 including specular surface normal, specular angle of anisotropy, specular roughness parameters, specular albedo, diffuse albedo, or diffuse normals.

9. The apparatus of claim 8, wherein the processor is configured to process and extract reflectance properties from one or more images of an object that includes at least one of translucent, transparent, or reflective surfaces.

10. The apparatus of claim 8, wherein the processor is configured to process the at least one image of the object to extract reflectance information using a multi-view stereo algorithm, and wherein the multi-view stereo algorithm uses at least one of specular and diffuse albedo or surface orientation measurements for geometry reconstruction.

11. The apparatus of claim 8, wherein the processor is configured to estimate the specular surface normal by:
determining a specular reflectance vector by reconstructing a reflectance function using a Spherical Harmonic basis, and finding a direction vector where the reconstruction attains a maximum value, wherein the Spherical Harmonic basis comprises one of a $3^{rd}$ order, a $4^{th}$ order, a $5^{th}$ order, or a higher order Spherical Harmonic basis;
rotating Spherical Harmonic responses to align the specular reflection vector to a zonal harmonic axis to produce zonal-aligned Spherical Harmonic responses; and
determining the specular surface normal using the determined specular reflectance vector.

12. The apparatus of claim 11, wherein the processor is further configured to:
rotate the zonal-aligned Spherical Harmonic responses around the zonal axis by an angle of anisotropy such that a −2 zonal-aligned Spherical Harmonic response is zero to produce anisotropy-aligned Spherical Harmonic responses;
determine the specular angle of anisotropy by finding half of an arctangent of a ratio of a +2 and −2 zonal-aligned Spherical Harmonic responses, wherein the zonal-aligned Spherical Harmonic responses comprise one of $3^{rd}$ order, $4^{th}$ order, or $5^{th}$ order zonal-aligned Spherical Harmonic responses; and
look up, in a first lookup table, the specular roughness parameters, using ratios computed from anisotropy-aligned measured Spherical Harmonic responses, wherein the first lookup table comprises a precomputed lookup table of major and minor specular roughness parameters, parameterized by a ratio of $5^{th}$ order to $3^{rd}$ order zonal harmonic response, and a ratio of +2 and zonal harmonic response, using synthetic rendering with a specular model of choice, and wherein the +2 and zonal harmonic response comprises one of $3^{rd}$ $4^{th}$ $5^{th}$ order, or higher order +2 and zonal harmonic response.

13. The apparatus of claim 12, wherein the processor is further configured to estimate the specular albedo at each surface point by:
looking up a nominal zonal harmonic in a second lookup table using the major and minor specular roughness parameters, wherein the second lookup table comprises a precomputed lookup table of zonal harmonic responses with unit specular albedo; and
finding the specular albedo as a ratio of a $3^{rd}$ order anisotropy-aligned measured Spherical Harmonic response to the nominal response from the second lookup table, wherein a nominal zonal harmonic comprises a zonal aligned response or one of $3^{rd}$, $4^{th}$ $5^{th}$ order, or higher order nominal zonal harmonic.

14. The apparatus of claim 12, wherein the processor is further configured to:
  synthesize a set of specular-only Spherical Harmonic responses using the specular normal, the specular angle of anisotropy, the specular roughness parameters and specular albedo, wherein synthesizing comprises using synthetic rendering or a lookup table;
  determine a set of diffuse-only Spherical Harmonic responses by subtracting the specular-only Spherical Harmonic responses from measured responses;
  determine a diffuse albedo as a product of a $0^{th}$ order diffuse-only Spherical Harmonic response and a normalizing constant, wherein the normalizing constant comprises 2/sqrt(Pi); and
  determine a diffuse normal as a vector with X, Y, and Z components equal to −1, 0, and +1 responses of $1^{st}$ order diffuse-only Spherical Harmonic responses, normalized to a unit vector.

15. The apparatus of claim 12, wherein each of the one or more cameras are calibrated using a single-shot camera calibration process including using a checkboard cylinder.

16. An apparatus for scanning an object to measure reflectance properties of the object, the apparatus comprising:
  a light source configured to illuminate the object with a controllable field of illumination including a series of different frequencies of illumination;
  one or more cameras, each camera configured to capture at least one image of the object; and
  a processor configured to process the at least one image to extract the reflectance properties of the object,
  wherein:
    processing the at least one image comprises extracting reflectance properties of the object including at least one of an albedo, a reflection vector, a roughness, and anisotropy parameters of a specular reflectance lobe associated with the object, and
    the controllable field of illumination comprises limited-order Spherical Harmonics (SH) or Fourier Series (FS) illumination patterns, wherein different light sources produce the SH illumination patterns and the FS illumination patterns.

17. The apparatus of claim 16, wherein:
  the one or more cameras comprise machine vision cameras,
  the one or more cameras are configured to employ exposure times long enough to integrate incident illumination from one of:
    a rotating arc of light generated by the light source,
    a flat panel light source configured to display a plurality of frequency patterns, or
    a closed surface source comprising a dome or a sphere that is illuminated with video patterns.

18. The apparatus of claim 16, wherein the light source comprises one of:
  a source assembly including a semi-circular arc shape or a polygon arc shape assembly comprising a plurality of light-emitting elements including light-emitting diodes (LEDs) and configured to rotate around the object to sweep a partial sphere surface or full sphere surface around the object and to illuminates the object with the SH illumination patterns,
  a flat panel light source configured to display a plurality of frequency patterns, to be moved to one or more positions to provide angular illumination over a wide field of view, and to illuminates the object with the SH illumination patterns, or a closed surface source comprising a dome or a sphere that is illuminated with video patterns.

19. The apparatus of claim 18, wherein the processor is configured to extract at least one of an albedo, a reflection vector, a roughness, and anisotropy parameters of a specular reflectance lobe associated with the object.

20. A method for determining the reflectance properties of an object comprising:
  Illuminating the object with a plurality of lighting conditions including a series of different frequencies of illumination;
  digitally photographing the object under the plurality of lighting conditions;
  analyzing digital photographs of the object taken under the plurality of lighting conditions to determine diffuse, specular, and specular roughness values at each surface point of the object; and
  creating the plurality of lighting conditions by one of:
    sweeping an array of light sources across an area including the object;
    modulating light intensities of light-emitting elements of an array of light-emitting elements to produce the plurality of lighting conditions;
    using a flat panel light source comprising a video display, wherein the flat panel source is configured to be moved to one or more positions to provide angular illumination over a wide field of view, and wherein the flat panel source is configured to illuminate the object with Fourier Series (FS) illumination patterns.

* * * * *